US012629121B2

(12) United States Patent
Tobón Gómez et al.

(10) Patent No.: US 12,629,121 B2
(45) Date of Patent: May 19, 2026

(54) METHOD OF DETERMINING VESSEL FLUID FLOW VELOCITY

(71) Applicant: Medis Associated B.V., Leiden (NL)

(72) Inventors: Catalina Tobón Gómez, Haarlem (NL); Hua Ma, Rotterdam (NL); Johannes Petrus Janssen, Leiden (NL); Gianni Pedrizzetti, Florence (IT); Johan Hendrikus Christiaan Reiber, Rotterdam (NL)

(73) Assignee: QFR Solutions B.V., Leiden (NL)

( * ) Notice: Subject to any disclaimer, the term of this patent is extended or adjusted under 35 U.S.C. 154(b) by 257 days.

(21) Appl. No.: 18/136,006

(22) PCT Filed: Oct. 20, 2021

(86) PCT No.: PCT/NL2021/050635
§ 371 (c)(1),
(2) Date: Apr. 18, 2023

(87) PCT Pub. No.: WO2022/086326
PCT Pub. Date: Apr. 28, 2022

(65) Prior Publication Data
US 2025/0032079 A1     Jan. 30, 2025

(30) Foreign Application Priority Data

Oct. 20, 2020    (NL) ..................................... 2026715

(51) Int. Cl.
A61B 6/50      (2024.01)
A61B 6/00      (2024.01)
G06T 7/00      (2017.01)

(52) U.S. Cl.
CPC .............. *A61B 6/504* (2013.01); *A61B 6/481* (2013.01); *A61B 6/486* (2013.01); *A61B 6/5217* (2013.01);
(Continued)

(58) Field of Classification Search
None
See application file for complete search history.

(56) References Cited

U.S. PATENT DOCUMENTS

| | | |
|---|---|---|
| 10,687,774 B2 | 6/2020 | Lautenschläger |
| 2004/0265393 A1 | 12/2004 | Unger et al. |

(Continued)

FOREIGN PATENT DOCUMENTS

| | | |
|---|---|---|
| CN | 113887463 A | 1/2022 |
| EP | 3660858 A1 | 6/2020 |

(Continued)

OTHER PUBLICATIONS

Mendonca, Ana Maria, and Aurelio Campilho. "Segmentation of retinal blood vessels by combining the detection of centerlines and morphological reconstruction." IEEE transactions on medical imaging 25.9 (2006): 1200-1213. (Year: 2006).*

(Continued)

*Primary Examiner* — Michelle M Entezari Hausmann
(74) *Attorney, Agent, or Firm* — Banner & Witcoff, Ltd.

(57) ABSTRACT

Image data of contrast dye in a vessel in a body is acquired for determining flow rate. Based on images acquired under and angle relative to one another, a three-dimensional model of the vessel is constructed and length of a vessel section is determined. A series of at least two images, apart in time, under a first angle is assessed for determining progress of a front of the dye bolus in the vessel in time. In the images, the vessel may be segmented and brightness or a derivative thereof over at least one of time and distance may be assessed to determine the front. Progress distance is mapped to the three-dimensional model, for example by mapping segments from the image to the model, to obtain a more (Continued)

300'

300"

accurate and natural distance of progress over time. Flow rate is determined by natural progress distance over progress time.

12 Claims, 4 Drawing Sheets

(52) U.S. Cl.
CPC .. *G06T 7/0016* (2013.01); *G06T 2207/30104* (2013.01)

(56) References Cited

U.S. PATENT DOCUMENTS

| | | | | |
|---|---|---|---|---|
| 2009/0016587 A1* | 1/2009 | Strobel | ..................... | G06T 7/20 382/130 |
| 2011/0150274 A1* | 6/2011 | Patwardhan | ............ | G06T 7/149 382/209 |
| 2013/0064435 A1* | 3/2013 | Taerum | ..................... | G06T 7/12 382/128 |
| 2015/0297373 A1* | 10/2015 | Schmitt | ..................... | A61F 2/86 623/1.16 |
| 2017/0140532 A1* | 5/2017 | Dascal | ..................... | G06T 5/50 |
| 2018/0099125 A1 | 4/2018 | Richer et al. | | |
| 2019/0029624 A1 | 1/2019 | Kunio | | |
| 2019/0365336 A1* | 12/2019 | Wagner | ..................... | G06T 5/94 |
| 2020/0175679 A1* | 6/2020 | Reiber | ..................... | G06T 19/00 |
| 2020/0219252 A1* | 7/2020 | Tsuyuki | ................. | A61B 6/488 |
| 2020/0222018 A1 | 7/2020 | van Walsum et al. | | |
| 2022/0343494 A1 | 10/2022 | Dhatt et al. | | |
| 2022/0378396 A1* | 12/2022 | Yoshida | ............. | G01S 7/52053 |

FOREIGN PATENT DOCUMENTS

| | | |
|---|---|---|
| JP | 2002534204 A | 10/2002 |
| JP | 2016159116 A | 9/2016 |
| JP | 2022-95470 A | 6/2022 |
| WO | 2019210553 A1 | 11/2019 |
| WO | 2022086326 A1 | 4/2022 |

OTHER PUBLICATIONS

XP019043569 (Hrvoje Bogunovic et al): "Blood Flow and Velocity Estimation Based on Vessel Transit Time by Combining 2D and 3D X-Ray Angiography", (Jan. 1, 2006)).

XP060008077 (Hentschke Clemens M et al): "Estimatingb lood flow velocity in angiographic image data", (Mar. 3, 2011), (bladzijden 1-9).

International Search Report and Written Opinion—PCT/NL2021/050635—mailing date Apr. 28, 2022.

Gibson et al, Circulation, 93, 5 (1996) 879-888.

* cited by examiner

200

200

METHOD OF DETERMINING VESSEL FLUID FLOW VELOCITY

CROSS-REFERENCE TO RELATED APPLICATIONS

This application is a U.S. National Stage application under 35 U.S.C. § 371 of International Application PCT/NL2021/050635 (published as WO 2022/086326 A1), filed Oct. 20, 2021 which claims the benefit of priority to Application NL 2026715, filed Oct. 20, 2020. Benefit of the filing date of these prior applications is hereby claimed. Each of these prior applications is hereby incorporated by reference in its entirety.

TECHNICAL FIELD

The various aspects and implementation thereof relate to the field of determining fluid flow velocity in a vessel of a body of a mammal, based on image acquired in a non-invasive way.

BACKGROUND

For determining various parameters of a cardiovascular system, like fractional flow reserve, flow velocity of blood in a coronary vessel may be required. The flow velocity may be determined as described in *"TIMI Frame Count"* by C. Michael Gibson e.a. as published in Circulation 1996; 93:879-888.

SUMMARY

It is preferred to provide a more accurate and standardised way of acquiring a value for flow velocity of a fluid through a vessel of a body of a living being and in particular of blood in a coronary vessel of a human being.

A first aspect provides a method of determining vessel fluid flow velocity of a fluid in a vessel segment of a body of a human or another mammal. The method comprises obtaining a natural length model of the vessel representing the length of the vessel, obtaining a two-dimensional model of the vessel segment and dividing the two-dimensional model in vessel sections and receiving a set of images including image data of the vessel sections, each image corresponding to a different moment in time. The method further comprises, based on the images of the set, assigning, for each image of the set, at least one intensity value to each vessel section, identifying, in a first image related to a first moment in time, a first vessel section, based on an intensity criterion, identifying, in a second image related to a second moment in time, a second vessel section, based on the intensity criterion, the second moment in time being later than the first moment in time and the second vessel section being distal to the first vessel section, obtaining a propagation length by relating the first vessel section and the second vessel section to the natural length and determining a vessel fluid flow velocity based on the propagation length and a difference between the first moment in time and the second moment in time.

This method provides an effective, objective and accurate way to determine the blood flow rate. In particular by transforming the 2D data to the 3D model, accuracy is improved. Such mapping may be applied to either distance or the finally determined flow rate. The difference between the first moment in time and the second moment in time may be based on the actual first moment and second moment, on a frequency of image acquisition or image availability, other entity indicating temporal difference between the first image and second image or any combination thereof.

In an embodiment, determining the natural length model comprises obtaining first two-dimensional image data of the vessel segment under a first angle, obtaining second two-dimensional image data of the vessel segment under a second angle, constructing a three-dimensional model of the vessel based on the first two-dimensional image and the second two-dimensional image and determining a length of the centreline of the three-dimensional model of the vessel. This implementation provides an accurate approximation of the real length of the vessel and with that, an accurate approximate of the flow rate may be obtained.

In another embodiment, obtaining the first two-dimensional image data comprises obtaining a first series of two-dimensional images acquired consecutively in time and obtaining the second two-dimensional image data comprises obtaining a second series of two-dimensional images acquired consecutively in time. Obtaining multiple images in time provides options for a further selection of images used to construction of the model.

In a further implementation, the set of images is selected from the first series of two-dimensional images or from the second series of two-dimensional images. Taking the set of images from one series provides a more accurate set of data.

In yet another implementation, a length of the vessel as depicted by the first series of two-dimensional images and the second series of two-dimensional images is determined and the set of images is selected from the series of two-dimensional images depicting the vessel with a longest length.

Most vessels and in particular a coronary vessel does not follow a straight path, but rather a path with many curves and bends. In particular if two sets of images are taken under an angle relative to one another, the vessel may be depicted longer under a first angle than under a second angle. With the vessel depicted with the longest length, a higher resolution may be obtained.

In again another implementation, dividing the two-dimensional model in vessel sections comprises defining volume sections along the centreline of the three-dimensional model of the vessel and mapping the volume sections to the series of images as vessel sections. In this way, the full volume of the vessel is divided, providing more data for analysis. In turn, this may provide more accuracy.

In yet a further embodiment, dividing the two-dimensional model in vessel sections comprises defining the vessel sections in the two-dimensional model and associating the vessel sections to points in the natural length model. With a two-dimensional mapping of a vessel having a three-dimensional shape based on two-dimensional image data, data may be lost. Such data may be recovered with this implementation.

In again a further implementation, associating the vessel sections to points in the natural length model comprises associating the vessel sections with volume sections along the centreline of the of the three-dimensional model of the vessel. The vessel may have variations in width and in particular in case of stenosis, the width may increase and decrease along the length. Influence of such variations is decreased with this implementation, by providing a centreline of the vessel rather than a local central point, locally in a lumen.

In a further implementation, the intensity criterion comprises a threshold value and the criterion is held to be met if the intensity of image data associated with a segment is at least one of more or less than the threshold value. This embodiment translates a continuous or semi-continuous scale to a binary scale. This increases computational efficiency.

In again a further implementation, the intensity criterion comprises a time derivative threshold value of the intensity value over time. A sudden increase of intensity or more in general, a sudden change of intensity, may provide a more accurate intensity of a change in intensity than the intensity being lower or higher than a particular threshold. Hence, this implementation provides increased accuracy.

Yet a further implementation further comprises normalising, for each vessel section, the intensity value over the images of the set. Intensity values may change over time and in implementations using contrast dye, such contrast dye may dilute over time. Such effects may be compensated using this implementation.

In again another implementation, the first two-dimensional image data and the second two-dimensional image data are obtained using x-ray. Whereas also MRI, CT and other image acquisition methods may be used, X-ray provides an advantage of using well proven technology and increased contrast which enables efficient data processing. It is noted that the first aspect and other embodiments thereof may also be applied to other techniques that provide a 3 dimensional representation of a vessel segment.

A second aspect provides a computer program comprising instructions which, when the program is executed by a computer, cause computer to carry out the method of the first aspect.

A third aspect provides a data processing device comprising a processor configured to perform the method of the first aspect.

BRIEF DESCRIPTION OF THE DRAWINGS

The various aspects and implementations thereof will now be discussed in further detail in conjunction with drawings. In the drawings:

FIG. 2 B: shows a second part of a flowchart;

DETAILED DESCRIPTION

Figure 1:
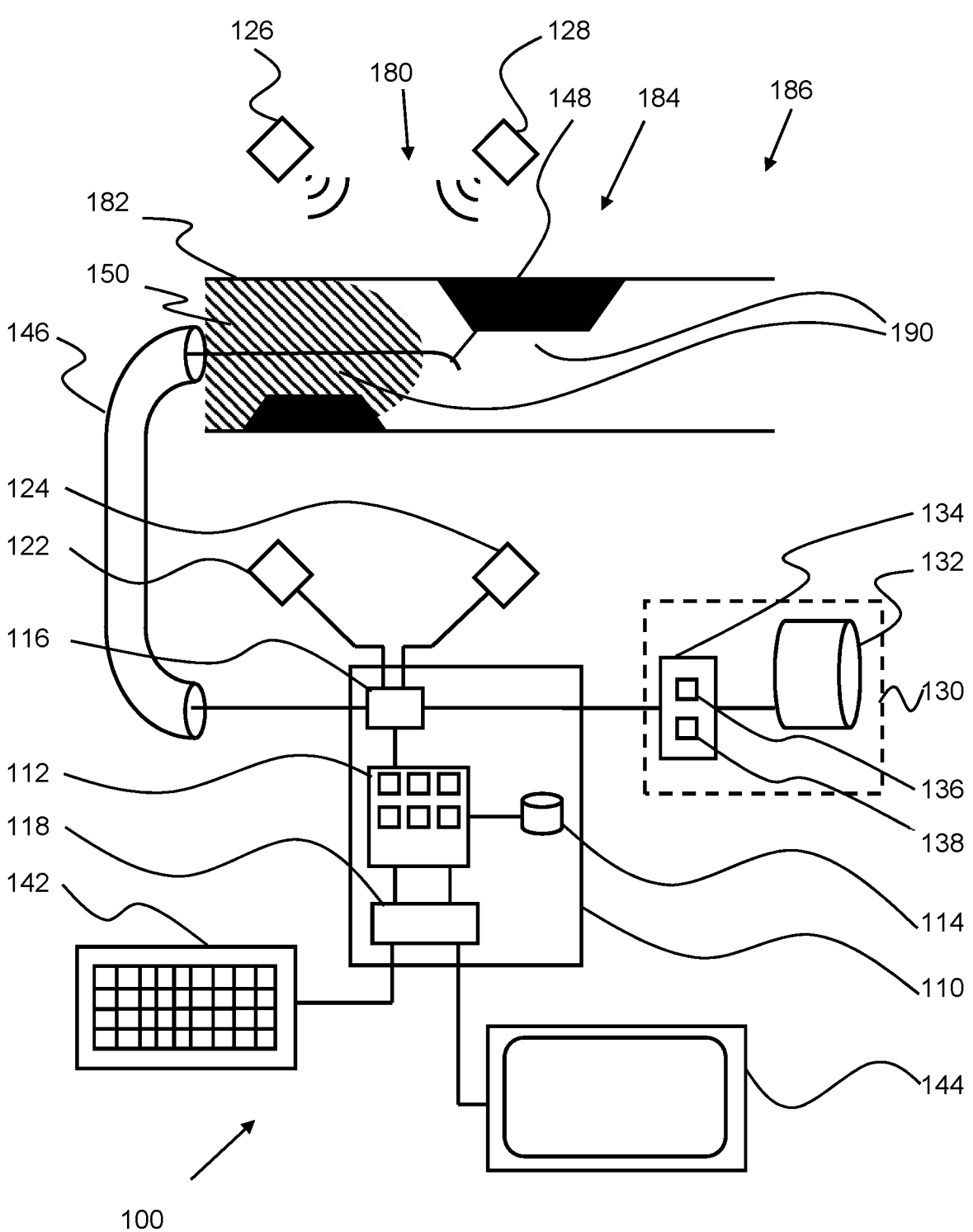
FIG. 1: shows a system for image acquisition and processing.

FIG. 1 shows an electronic medical data acquisition and processing system 100 as an example of the second aspect. The system 100 or parts thereof may be found in a cardiac catheterisation laboratory of a clinic or a hospital. The system 100 comprises an X-ray image acquisition module comprising a first X-ray source 126 and a second X-ray source 128, a first X-ray detector 122 arranged to receive X-ray data from the first X-ray source 126 and a second X-ray sensor 124 arranged to receive X-ray data from the second X-ray source 128. The first X-ray source 126, the second X-ray sensor 124, the first X-ray detector 122 and the second X-ray sensor 124 are arranged to obtain images of a cardiovascular structure 180 under an angle relative to one another. The angle is preferably between 25° and 45°, more preferably between 30° and 40°.

The first X-ray detector 122 and the second X-ray detector 124 are connected to data acquisition module 116 of an electronic computing device 110. The electronic computing device further comprises a processing unit 112, a storage module 114 and a peripherals I/O controller 118. The processing unit 112, which may be implemented as a microprocessor, microcontroller or other electronic data processing device, is arranged to control the various part of the electronic computing device 110 and the system 100 and arranged to execute the method according to the first aspect and implementations thereof.

The storage module 114 is arranged for storing data thereon, for example acquired by the computing device 110 from the various other parts of the system 100, either directly or after processing by the processing unit 112. The storage unit 114, as at least partially implemented as a non-transitional storage medium, is further arranged for storing computer executable code which allow the processing unit 112 to execute the method according to the first aspect and implementations thereof.

The system 100 further comprises, in this implementation as an option, a first blood pressure measurement module 130 comprising a pressure cuff 132 and a control unit 134 comprising a pulse sensor 136 and a pressure control unit 138 arranged to control air pressure in the pressure cuff 132 by inflating and deflating the pressure cuff 132.

The system 100 comprises a pressure tip 148 as a another blood pressure measurement module, which corresponds to the intracoronary distal pressure. The pressure tip 148, which is connected to a coronary wire, transmits the pressure to the data acquisition module 116, from a coronary artery 182 of the cardiovascular structure 180 as an example of a coronary vessel or blood vessel in general via a catheter 146 inserted in a body of a mammal, like a human being. Additionally, the tip of the coronary catheter 146, placed into the ostium of the coronary artery under scrutiny 182, sense the proximal pressure into the vessel, which corresponds to the aortic pressure. Furthermore, the catheter 146 may be used to insert contrast dye 150 in the coronary artery 182 or another vessel of a body.

The peripherals I/O controller 118 is arranged to connect the computing device 110 and the various components thereof to input device like a keyboard 142 or a touch screen for receiving data like user input. The peripherals I/O controller 118 is arranged to connect the computing device 110 and the various components thereof to output devices like an electronic display 144 and other output devices arranged to provide a user with data on processed or unprocessed data received by the computing device 110.

As shown in FIG. 1, the catheter 146 and the pressure wire 148 are inserted in the coronary artery 182. In the coronary artery 182, narrowings 190 are present. The stenotic areas result in narrowing in the various vessels of the coronary vascular structure 180, which, in turn results in pressure drops at the various stenotic areas. Subsequently, the pressure drops result in reduced perfusion of myocardial tissues, which leads to reduced physical condition of the person under scrutiny. The cardiovascular structure 180 shown by FIG. 1 may be a hypothetical structure and is not necessarily a representation of an actual anatomical structure.

Figure 2:
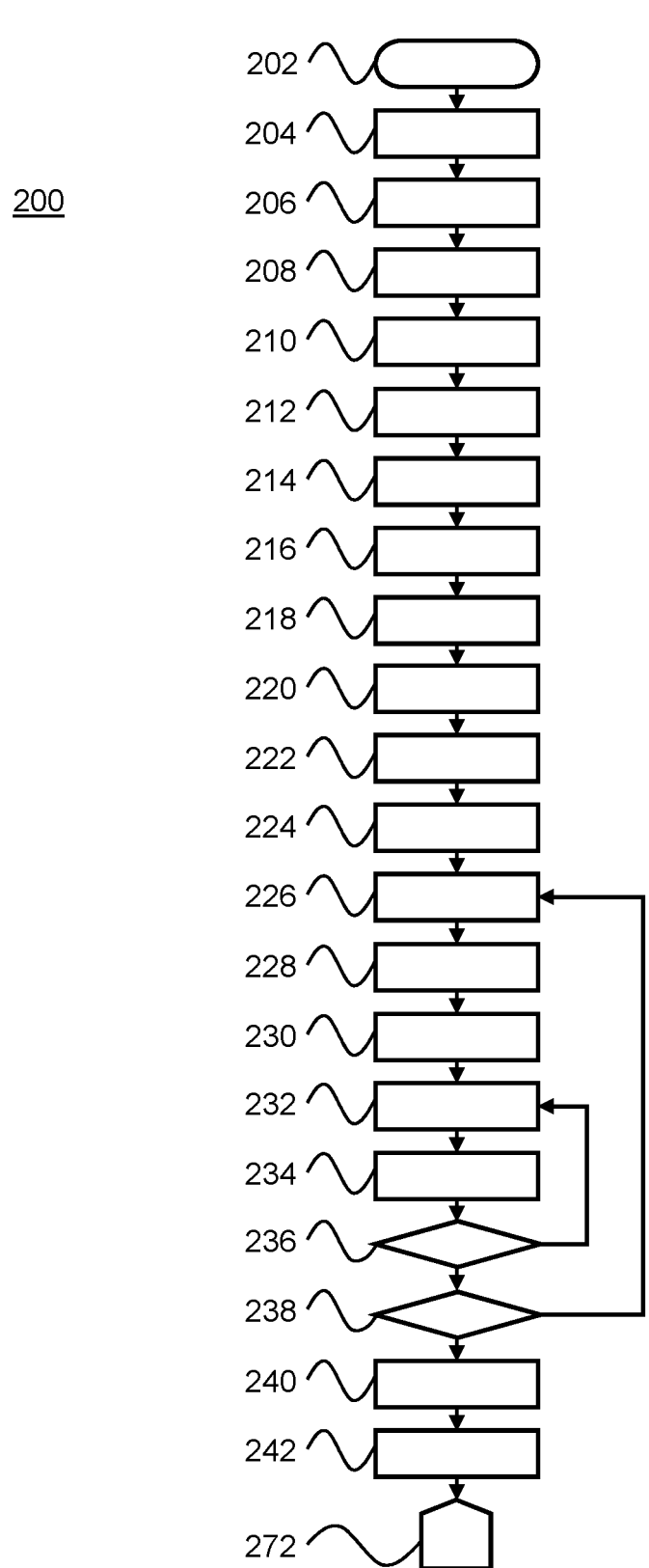
FIG. 2 A: shows a first part of a flowchart.
Figure 2:
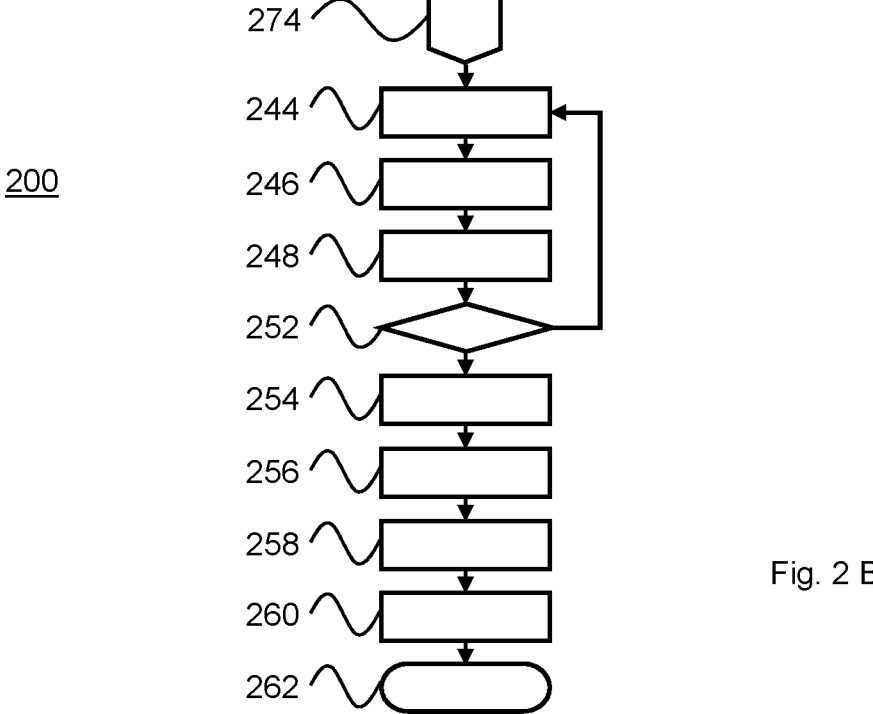

The further functionality of the system 100 and parts thereof discussed above will be further elucidated in conjunction with a flowchart 200 depicted by FIG. 2 A and FIG. 2 B. The procedure depicted by the flowchart 200 is executed by the system 100 and the electronic computing device 110 in particular, controlled by the processing unit 112. The various parts of the flowchart 200 are briefly summarised below.

202 Start procedure
204 Obtain first image series

Figure 3:
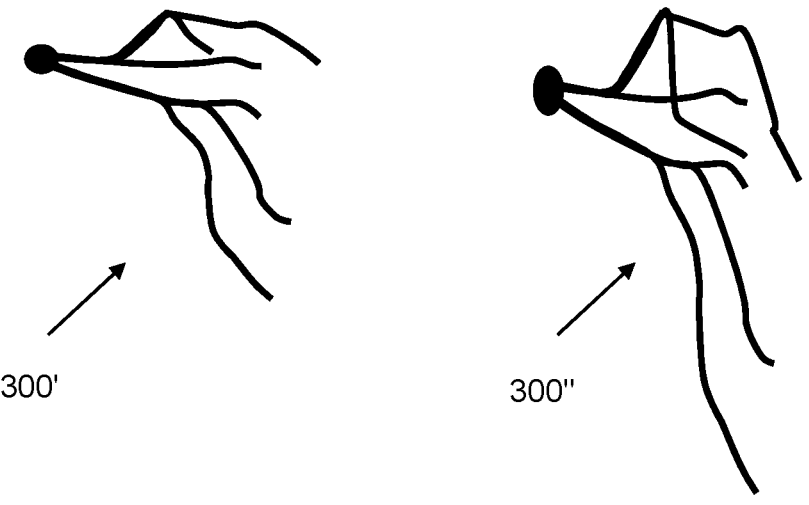
FIG. 3: shows two images of a cardiovascular structure.

206 Obtain second image series
208 Obtain first image from first series
210 Obtain second image from second series
212 Construct 3D model
214 Obtain vessel selection
216 Determine length of selected vessel
218 Received selection criterion
220 Select one of two sets
222 Construct 2D model
224 Segment 2D model
226 Obtain image from selected set
228 Identify selected vessel
230 Segment identified vessel
232 Analyse intensity values in segment
234 Assign intensity value to segment
236 All segments done?
238 All images done?
240 Normalise intensity data
242 Obtain threshold data
244 Obtain normalised image
246 Assess intensity to threshold data
248 Determine front
250 Map front to 3D length data
252 All images done?
254 Select two images
256 Obtain time between two images
258 Obtain 3D length between fronts
260 Determine propagation speed
262 End The procedure starts in a terminator 202. At the start of the procedure, the contrast dye 150 is inserted at the proximal end of the coronary artery 182. The procedure continues in step 204 for obtaining a first series of images, which images are distributed over time by means of the first X-ray detector 122, while the contrast dye 150 progresses through the coronary artery 182 over time. FIG. 3 shows, at the left, a first image 300' as an example of the last image or one of the last images of the first series of images, in which the vessels of the cardiovascular structure 180 are filled with the contrast dye.

In step 206, a second series of images is taken, preferably by means of the first X-ray detector 124, in an analogous fashion as the first series is obtained. The first series is preferably obtained at the same moment the second series is obtained. FIG. 3 shows, at the left, a second image 300" as an example of the last image or one of the last images of the second series of images, in which the vessels of the cardiovascular structure 180 are filled with the contrast dye. In case only one X-ray source and only one X-ray image sensor are available in a laboratory, the second series of images will have to be acquired after the first series has been acquired, with a second dose of contrast dye to be inserted in the cardiovascular structure 180.

In step 208, a first image of the first series is selected for constructing a three-dimensional model of the cardiovascular structure 180 or in any case of the coronary artery 182 under scrutiny. The first image may be selected as disclosed by European patent application published with number EP3660858. In step 210, a second image is selected from the second series and in step 212, a three-dimensional model of the cardiovascular structure 180 or in any case of the coronary artery 182 under scrutiny is constructed.

The three-dimensional model may comprise only a centreline of the coronary artery 182, a volumetric model, another model or a combination thereof. The three-dimensional model is constructed such that a length of the coronary artery 182 may be determined, preferably a true or natural length; a length of the coronary artery 182 obtained from a single, two-dimensional image of one of the two series may not be the actual length of coronary artery 182 as such arteries usually do not follow a straight path parallel to the image plane.

In step 214, a selection is received of a vessel of which the length is to be determined. Such selection may be part of an automated process or may be retrieved by means of the keyboard 142 or a touch screen or another input device. In this example, the coronary artery 182 is selected. In some processes, only the coronary artery 182 is provided with the contrast dye 150, which makes automatic detection of the coronary artery 182 more efficient. Subsequently, in step 216, the length of the coronary artery 182. Such may be done by determining the length of the centreline from the proximal point to the most distal point at which contrast dye is detected. Alternatively or additionally, a length of an outer contour of the vessel under scrutiny may be determined in the three-dimensional model. It is noted that the steps 212 through 216 may be executed in parallel to subsequent steps, following step 256 or any other step prior to step 258.

In step 218, a selection criterion is received for choosing either the first selected image from the first series or the second selected image of the second series to select the previously constructed two-dimensional model of the vessel under scrutiny. Alternatively, another image may be selected, from either the first image series or the second image series.

Preferably, such image is an image at which the vessel under scrutiny is fully or at least for the vast majority filled with the contrast dye 150. Preferably, the selection criterion favours an image in which the vessel under scrutiny is the longest. Alternatively or additionally, input for selecting an image is received by means of the keyboard 142 or a touch screen or another input device; such may be a direct input selecting the image. In step 220, the image satisfying the selection criterion or selection criteria is selected.

In step 222, a two-dimensional model of the vessel under scrutiny is constructed, based on the selected image. The two-dimensional model may comprise only a centreline of the coronary artery 182, a volumetric model, another model or a combination thereof. The two-dimensional model may be constructed here or, alternatively or additionally, be constructed prior to constructions of the 3D model in step 212.

In step 224, the two-dimensional model of the vessel under scrutiny is segmented. The segmentation may depend on the structure of the model; if the model comprises only a centreline, the segmentation may comprise identifying at least one of the points on the line or line sections. If the model comprises one or more of areas or volumes, optionally defined around a centreline, the segmentation may comprise defining at least one of the sub-areas or volume sections, optionally along the centreline. The sub-areas and volume sections may be directly adjacent or at distances from one another. Alternatively or additionally, the segmentation may also in such scenario comprise identifying line segments or points within the model. Alternatively or additionally, the segmentation is applied to every image or every image selected for this purpose. Prior to the segmentation of a particular vessel, a vascular tree of which the particular vessel is a part may be segmented first, in separate vessels and/or parts thereof.

In step 226, an image, preferably a first image in a time sequence, is obtained from the first set. In step 228, the vessel under scrutiny is identified, or at least part thereof that is already filled with contrast dye 150. In step 230, the identified vessel is segmented in accordance with the segmentation defined in step 224 at every image of the time sequence. In one implementation, the vessel is only tracked or identified in frames preceding the selected image frame. This example improves computations efficiency.

In step 232, intensity values in each segment are analysed. The image acquired is preferably acquired in a digital electronic way, which means that the image is build up from pixels. In this scenario, each pixel does not have a colour value or values with intensities for three or more colours, but only one intensity value as is common with medical imaging techniques like MRI, CT and X-ray. In case the acquired images are analogue, the images are digitised in an electronic format.

Depending on the segmentation, a segment comprises one or more pixels. In case segments are defined as points, pixels surrounding the points with less than a pre-determined distance may be assigned to the closest point. With multiple pixels and hence, multiple intensity values assigned to a segment, the intensity values are analyses to determine one intensity value for the segment. This may be executed using one or more statistical operations, including, but not limited to, at least one of calculating a mean value, an average value, determining standard deviation, before executing any of these operations; outliers may be removed if they are more than a particular percentage away from the average or the median or more than a factor of the standard deviation away from the average or the median value.

In step 234, the determined intensity value for the segment is assigned to the segment. In step 236, the procedure checks whether any further segments may be identified in the image under processing. If this is the case, the procedure branches back to step 232. If not, the procedure continues to step 238, in which step the procedure checks whether any further image in the selected series are to be processed. If this is the case, the procedure branches back to step 226. If all images have been processed, the procedure proceeds to the next step. It is noted that not all acquired images need to be processed; it may be sufficient to process only a part of the set: every second, third, fourth, tenth, twentieth or nth image may be sufficient. In an ultimate case, only two images are processed.

Once the required or otherwise determined amount of images has been processed as described above, the data may be normalised in step 240. Preferably, the data of the processed images and the intensity values in particular are normalised time-wise, i.e. over time. The standard for normalisation may be based on a mean or median value of intensity of one or more particular segments, over one or more images, a particular fixed value, other, or a combination thereof. The result of the processing is shown in FIG. 4.

Figure 4:
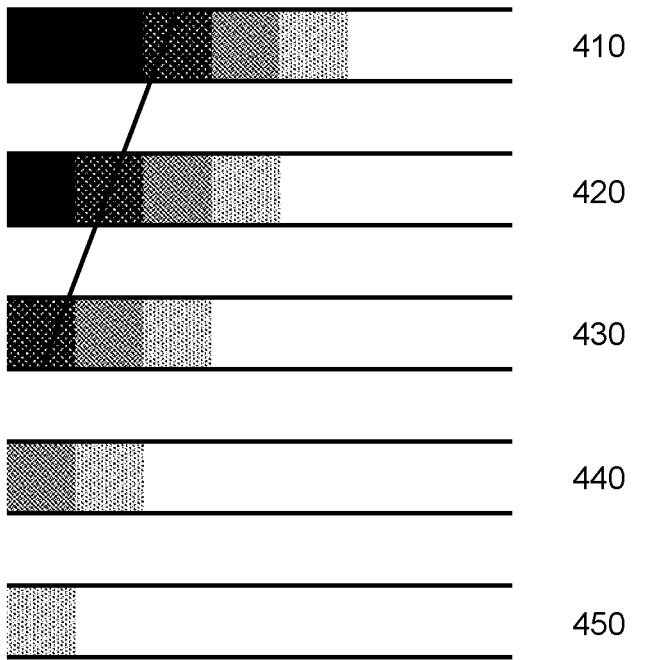
FIG. 4: shows sets of processed data values.

FIG. 4 shows normalised intensity values assigned to sections a vessel under scrutiny; normalised intensity values are shown for a first location 410, a second location 420, a third location 430, a fourth location 440 and a fifth location 450. The first location is more proximal than the fifth location. A darker shade indicates a higher concentration of contrast dye 150 in the vessel under scrutiny. Time, from one frame to a subsequent frame, is indicated from left to right.

In FIG. 4, colour intensities are depicted such that white indicates no presence of contrast dye and black indicates presence of contrast dye. In another embodiment, images are taken in negative compared to the embodiment shown by FIG. 4; in such alternative embodiment, white indicates presence of contrast dye and black indicates no presence of contrast dye.

Once the data has been normalised, threshold data is obtained in step 242. The threshold data may comprise a particular fixed intensity value or a particular intensity value adjusted in accordance with the normalisation procedure discussed above. Alternatively or additionally, the threshold data may comprise data and criteria in particular for change of intensity values over at least one of time or from one segment to one or more other segment in at least one of the same or other images.

In the latter case, compliance of the threshold criterion may be determined by determining change of acquired intensity values over vessel distance or from frame to frame over time, i.e. determining a derivative of the intensity value as a function of time or location in the vessel. In step 244, a normalised image from a series of normalised—or not normalised—images is obtain. With the data thus obtained, the procedure continues to step 246, in which the intensity data in the image is assessed to the threshold data.

As a result of the assessment, it is in step 248 be determined at which segment or which segments the threshold criterion is satisfied; such segment or segments are identified as being associated with a front of a bolus of contrast dye 150. In step 250, the segment at which the front is determined to be for the particular image is mapped to a location in the three-dimensional model for determining a distance between the segment with the front and a fixed location of the vessel under scrutiny, for example the most proximal point. Alternatively, the mapping from segments in the two-dimensional model to a distance value in the three-dimensional model has been executed earlier in the procedure.

In step 252, the procedure checks whether all images required for determining flow speed have been assessed. If this is not the case, the process branches back to step 244. If all images have been processed, the procedure continues to step 254, in which two images are selected or at least data from two images is retrieved. The data retrieved from the processed images are the distance of the front relative to a fixed point in the vessel under scrutiny.

In step 256, a time difference between the two images 254 is obtained. The time difference may be available as such. Alternatively, the time difference may be obtained using values as image acquisition speed and frame distance between two applicable images. If images have been acquired as 20 frames per second and images are 34 frames apart, the time difference is 1.7 seconds.

In step 258, the distance between the fronts in the two images is determined. With the distance of the dye front to the fixed point, like the most proximal point of the vessel, known for both images, the distance may be determined by subtracting both values—the smallest from the largest in this implementation. The distance thus obtained divided by the time period, obtained in step 256, determines the propagation speed of contrast dye and with that, of blood through the vessel under scrutiny. Subsequently, the procedure ends in terminator 262.

In summary, image data of contrast dye in a vessel in a body is acquired for determining flow rate. Based on images acquired under and angle relative to one another, a three-dimensional model of the vessel is constructed and length of a vessel section is determined. A series of at least two images, apart in time, under a first angle is assessed for determining progress of a front of the dye bolus in the vessel in time. In the images, the vessel may be segmented and brightness or a derivative thereof over at least one of time and distance may be assessed to determine the front. Progress distance is mapped to the three-dimensional model, for example by mapping segments from the image to the model, to obtain a more accurate and natural distance of progress over time. Flow rate is determined by natural progress distance over progress time.

The invention claimed is:

1. A method of determining vessel fluid flow velocity of a fluid in a vessel segment of a body of a human or another mammal, the method comprising:

obtaining first two-dimensional image data of the vessel segment under a first angle and obtaining second two-dimensional image data of the vessel segment under a second angle, to determine a natural length model of the vessel representing a length of the length of the vessel, wherein the first two dimensional image data are obtained from a first series of two-dimensional images acquired consecutively in time and the second two-dimensional image data are obtained from a second series of two-dimensional images acquired consecutively in time;

obtaining a two-dimensional model of the vessel segment;

dividing the two-dimensional model in vessel sections;

selecting a set of images from the first series of two-dimensional images or from the second series of two-dimensional images, based on the series depicting the vessel with a longest length, wherein the set of images includes image data of the vessel sections, each image corresponding to a different moment in time;

based on the images of the set, assigning, for each image of the set, at least one intensity value to each vessel section;

identifying, in a first image related to a first moment in time, a first vessel section, based on an intensity criterion;

identifying, in a second image related to a second moment in time, a second vessel section, based on the intensity criterion, the second moment in time being later than the first moment in time and the second vessel section being distal to the first vessel section;

obtaining a propagation length by relating the first vessel section and the second vessel section to the natural length; and determining a vessel fluid flow velocity based on the propagation length, and a difference between the first moment in time and the second moment in time.

2. The method according to claim 1, wherein determining the natural length model further comprises:

constructing a three-dimensional model of the vessel based on the first two-dimensional image and the second two-dimensional image; and determining a length of the centreline of the three-dimensional model of the vessel.

3. The method according to claim 1, wherein the set of images is acquired under the first angle or the second angle.

4. The method according to claim 2, wherein dividing the two-dimensional model in vessel sections comprises:

defining volume sections along the centreline of the of the three-dimensional model of the vessel; and mapping the volume sections to the series of images as vessel sections.

5. The method according to claim 1, wherein dividing the two-dimensional model in vessel sections comprises:

defining the vessel sections in the two-dimensional model; and associating the vessel sections to points in the natural length model.

6. The method according to claim 5, wherein determining the natural length model comprises:

obtaining first two-dimensional image data of the vessel segment under a first angle;

obtaining second two-dimensional image data of the vessel segment under a second angle;

constructing a three-dimensional model of the vessel based on the first two-dimensional image and the second two-dimensional image;

determining a length of the centreline of the three-dimensional model of the vessel; and associating the vessel sections to points in the natural length model comprises associating the vessel sections with volume sections along the centreline of the three-dimensional model of the vessel.

7. The method according to claim 1, wherein the intensity criterion comprises a threshold value and the criterion is held to be met if the intensity of image data associated with a segment is at least one of more or less than the threshold value.

8. The method according to claim 1, wherein the intensity criterion comprises a time derivative threshold value of the intensity value over time.

9. The method according to claim 1, further comprising normalising, for each vessel section, the intensity value over the images of the set.

10. The method according to claim 2, wherein the first two-dimensional image data and the second two-dimensional image data are obtained using x-ray.

11. A non-transitory computer-readable medium comprising instructions for causing a processor to carry out the method of claim 1.

12. A data processing device comprising a processor adapted to perform the method of claim 1.

* * * * *